United States Patent [19]

Sih

[11] 4,284,792

[45] Aug. 18, 1981

[54] 19-HYDROXY-19-METHYL-INTER-PHENYLENE-PG$_1$ COMPOUNDS

[75] Inventor: John C. Sih, Kalamazoo, Mich.

[73] Assignee: The Upjohn Company, Kalamazoo, Mich.

[21] Appl. No.: 133,200

[22] Filed: Mar. 24, 1980

Related U.S. Application Data

[62] Division of Ser. No. 25,878, Apr. 2, 1979, Pat. No. 4,228,104.

[51] Int. Cl.$^3$ .......................................... C07C 177/00
[52] U.S. Cl. ...................................... 560/55; 560/53; 562/463; 562/465
[58] Field of Search ................... 560/53, 55; 562/463, 562/465

[56] References Cited

PUBLICATIONS

Derwent Abstract 79369Y/45, BE 854271, 04-11-77.
Derwent Abstract 69387Y/39, J5 0112-338, 03-09-75.
Derwent Abstract 89537A/49, US 4127-612, 28-11-78.
Derwent Abstract 01868W/01, US 3856-852, 24-12-74.

Primary Examiner—Paul J. Killos
Attorney, Agent, or Firm—Robert A. Armitage

[57] ABSTRACT

The present invention provides novel 19-hydroxy-19-methyl-inter-phenylene-PG$_1$ compounds, methods for their preparation and pharmacological use for the induction of prostaglandin-like effect.

2 Claims, No Drawings

19-HYDROXY-19-METHYL-INTER-PHENYLENE-PG$_1$ COMPOUNDS

CROSS REFERENCE TO RELATED APPLICATIONS

The present application is a division of Ser. No. 025,878, filed Apr. 2, 1979, now U.S. Pat. No. 4,228,104.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-19-methyl-PG compounds. Most particularly, the present invention relates to novel 19-hydroxy-19-methyl-inter-phenylene-PG$_1$ compounds, a disclosure of the preparation and use of which is incorporated here by reference from U.S. Pat. No. 4,228,104.

Prior Art

Prostaglandin analogs exhibiting hydroxylation in the 19-position are known in the art. See, for example, U.S. Pat. No. 4,127,612, Sih, J. C., Prostaglandins 13:831 (1977) and U.S. Pat Nos. 3,657,316, 3,878,046, and 3,922,297. See also the additional references cited in U.S. Ser. No. 025,878.

SUMMARY OF THE INVENTION

The present invention particularly provides:
a compound of the formula

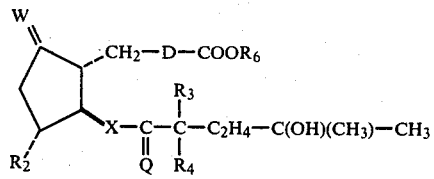

wherein D is
(1) —(m—Ph)—(CH$_2$)$_2$—, or
(2) —(m—Ph)—O—CH$_2$—,
wherein —(m—Ph)— is inter-meta-phenylene, and
wherein Q is $\alpha$-OH:$\beta$-R$_5$ or $\alpha$-R$_5$:$\beta$-OH, wherein R$_5$ is hydrogen or methyl;
wherein R$_6$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive,
(g) —(p—Ph)—CO—CH$_3$,
(h) —(p—Ph)—NH—CO—(p—Ph)—NH—CO—CH$_3$,
(i) —(p—Ph)—NH—CO—(p—Ph),
(j) —(p—Ph)—NH—CO—CH$_3$,
(k) —(p—Ph)—NH—CO—NH$_2$,
(l) —(p—Ph)—CH=N—NH—CO—NH$_2$,
(m) $\beta$-naphthyl,
(n) —CH$_2$—CO—R$_{28}$,
wherein (p—Ph) is para-phenyl or inter-para-phenylene,
wherein R$_{28}$ is phenyl, p-bromophenyl, p-biphenylyl, p-nitrophenyl, p-benzamidophenyl, or 2-naphthyl, or
(o) a pharmacologically acceptable cation;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, $\alpha$-OH:$\beta$-H, or $\alpha$-H:$\beta$-OH; and
wherein X is cis- or trans-—CH=CH— or —C≡C—.

With regard to the divalent the substituents described above (e.g., Q) these divalent radicals are defined as $\alpha$-R$_i$:$\beta$-R$_j$, wherein R$_i$ represents the substituent of the divalent moiety in the alpha configuration with respect to the ring and R$_j$ represents the substituent of the divalent moiety in the beta configuration with respect to the plane of the ring. Accordingly, when Q is defined as $\alpha$-OH:$\beta$-R$_5$, the hydroxy of the Q moiety is in the alpha configuration, i.e., as in the natural prostaglandin, and the R$_5$ substituent is in the beta configuration.

Specific embodiments of the present invention include:
19-hydroxy-19-methyl-3,7-inter-m-phenylene-PGF$_1\alpha$.

The compounds of the present invention are particularly useful for inducing prostaglandin-like biological effects, as is described in U.S. Ser. No. 025,878. Uses of compounds in accordance with the present invention include, therefore, anti-asthmatic indications.

I claim:
1. A compound of the formula

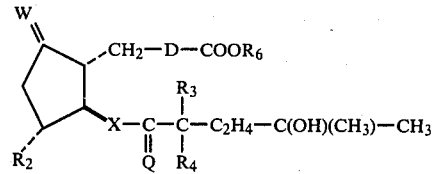

wherein D is
(1) —(m—Ph)—(CH$_2$)$_2$—, or
(2) —(m—Ph)—O—CH$_2$—,
wherein —(m—Ph)— is inter-meta-phenylene, and
wherein Q is $\alpha$-OH:$\beta$-R$_5$ or $\alpha$-R$_5$:$\beta$-OH, wherein R$_5$ is hydrogen or methyl;
wherein R$_6$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive,
(g) —(p—Ph)—CO—CH$_3$,
(h) —(p—Ph)—NH—CO—(p—Ph)—NH—CO—CH$_3$,
(i) —(p—Ph)—NH—CO—(p—Ph),
(j) —(p—Ph)—NH—CO—CH$_3$,
(k) —(p—Ph)—NH—CO—NH$_2$,
(l) —(p—Ph)—CH=N—NH—CO—NH$_2$,
(m) $\beta$-naphthyl,
(n) —CH$_2$—CO—R$_{28}$,
wherein (p—Ph) is para-phenyl or inter-para-phenylene,
wherein R$_{28}$ is phenyl, p-bromophenyl, p-biphenylyl, p-nitrophenyl, p-benzamidophenyl, or 2-naphthyl, or
(o) a pharmacologically acceptable cation;

wherein $R_2$ is hydrogen, hydroxyl, or hydroxymethyl;

wherein $R_3$ and $R_4$ are hydrogen, methyl, or fluoro, being the same or different, with the proviso that one of $R_3$ and $R_4$ is fluoro only when the other is hydrogen or fluoro;

wherein W is oxo, methylene, $\alpha$-OH:$\beta$-H, or $\alpha$-H:$\beta$-OH; and wherein X is cis- or trans—CH=CH— or —C≡C—.

2. 19(R)-19-hydroxy-19-methyl-3,7-inter-m-phenylene-PGF$_1\alpha$, a compound according to claim 1.

* * * * *